(12) United States Patent
Reddy et al.

(10) Patent No.: US 10,442,769 B2
(45) Date of Patent: Oct. 15, 2019

(54) PROCESS FOR THE PREPARATION OF INTERMEDIATE OF DOLUTEGRAVIR

(71) Applicant: HETERO RESEARCH FOUNDATION, Hyderabad (IN)

(72) Inventors: Bandi Parthasaradhi Reddy, Hyderabad (IN); Kura Rathnakar Reddy, Hyderabad (IN); Dsari Muralidhara Reddy, Hyderabad (IN); Mogili Narsingam, Hyderabad (IN); Bandi Vamsi Krishna, Hyderabad (IN)

(73) Assignee: Hetero Research Foundation (IN)

( * ) Notice: Subject to any disclaimer, the term of this patent is extended or adjusted under 35 U.S.C. 154(b) by 15 days.

(21) Appl. No.: 15/882,317

(22) Filed: Jan. 29, 2018

(65) Prior Publication Data

US 2018/0148412 A1   May 31, 2018

Related U.S. Application Data

(60) Division of application No. 14/968,088, filed on Dec. 14, 2015, now Pat. No. 9,963,430, which is a continuation of application No. PCT/IN2014/000444, filed on Jul. 3, 2014.

(30) Foreign Application Priority Data

Jul. 4, 2013   (IN) .......................... 2996/CHE/2013

(51) Int. Cl.
| | | |
|---|---|---|
| *C07C 231/02* | (2006.01) |
| *C07D 213/14* | (2006.01) |
| *C07D 213/69* | (2006.01) |
| *C07D 213/79* | (2006.01) |
| *C07D 213/80* | (2006.01) |
| *C07D 213/81* | (2006.01) |
| *C07D 213/82* | (2006.01) |
| *C07D 309/40* | (2006.01) |
| *C07D 498/12* | (2006.01) |

(52) U.S. Cl.
CPC .......... *C07D 213/82* (2013.01); *C07C 231/02* (2013.01); *C07D 213/14* (2013.01); *C07D 213/69* (2013.01); *C07D 213/79* (2013.01); *C07D 213/80* (2013.01); *C07D 213/81* (2013.01); *C07D 309/40* (2013.01); *C07D 498/12* (2013.01)

(58) Field of Classification Search
None
See application file for complete search history.

(56) References Cited

U.S. PATENT DOCUMENTS

| | | |
|---|---|---|
| 8,129,385 B2 | 3/2012 | Johns et al. |
| 8,217,034 B2 | 7/2012 | Johns et al. |
| 8,624,023 B2 | 1/2014 | Yoshida et al. |

FOREIGN PATENT DOCUMENTS

| | | |
|---|---|---|
| WO | 2010011812 A1 | 1/2010 |
| WO | 2010011819 A1 | 1/2010 |
| WO | 2010068253 A1 | 6/2010 |

*Primary Examiner* — Zinna Northington Davis
(74) *Attorney, Agent, or Firm* — Caesar Rivise, PC

(57) ABSTRACT

The present invention provides a novel processes for preparation of methyl 3-(benzyloxy)-5-(2,4-difluorobenzylcarbamoyl)-4-oxo-1-(2-oxoethyl)-1,4-dihydropyiridine-2-carboxylate using novel intermediates.

4 Claims, No Drawings

PROCESS FOR THE PREPARATION OF INTERMEDIATE OF DOLUTEGRAVIR

This application is a Divisional of U.S. Ser. No. 14/968,088 filed Dec. 14, 2015, which is a Continuation of PCT/IN2014/000444 filed Jul. 3, 2014, which claims the benefit of Indian Provisional Patent Application No. 2996/CHE/2013, filed on Jul. 4, 2013, which are all incorporated herein by reference.

FIELD OF THE INVENTION

The present invention provides a novel processes for preparation of methyl 3-(benzyloxy)-5-(2,4-difluorobenzyl-carbamoyl)-4-oxo-1-(2-oxoethyl)-1,4-dihydropyiridine-2-carboxylate using novel intermediates.

BACKGROUND OF THE INVENTION

Dolutegravir, chemically (4R,12aS)—N-(2,4-difluorobenzyl)-7-hydroxy-4-methyl-6,8-dioxo-3,4,6,8,12,12a-hexahydro-2H-pyrido[1',2':4,5]pyrazino[2,1-b][1,3]oxazine-9-carboxamide and has the structural formula I:

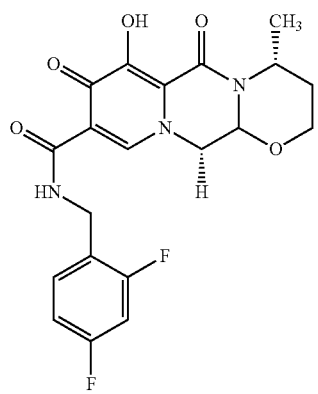

Dolutegravir is an experimental new drug under investigation for the treatment of HIV infection. Dolutegravir is an integrase inhibitor. Also known as S/GSK1349572 or, the drug is under development by GlaxoSmithKline (GSK).

The chemical formula of methyl 3-(benzyloxy)-5-(2,4-difluorobenzylcarbamoyl)-4-oxo-1-(2-oxoethyl)-1,4-dihydropyiridine-2-carboxylate of formula II:

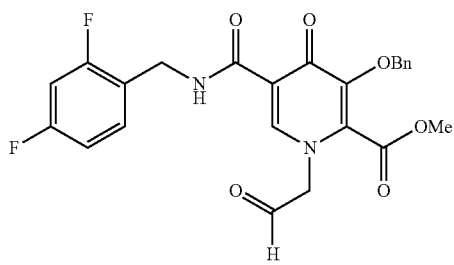

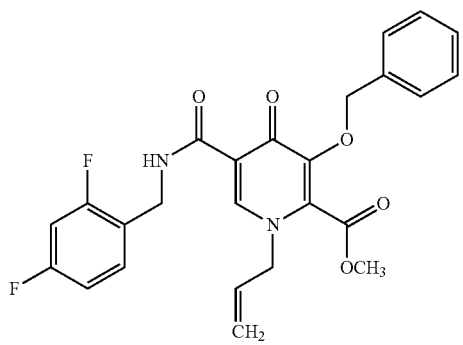

Dolutegravir and its processes were disclosed in U.S. Pat. No. 8,129,385 ('385 patent). The synthetic procedure is illustrated in scheme I, below:

Scheme I

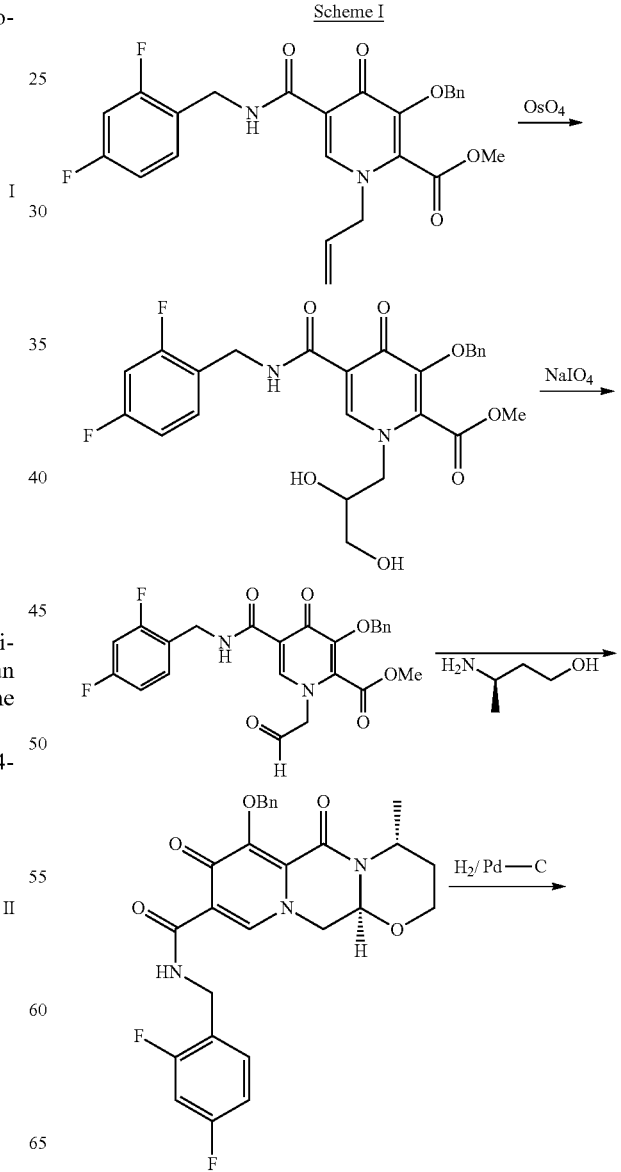

-continued

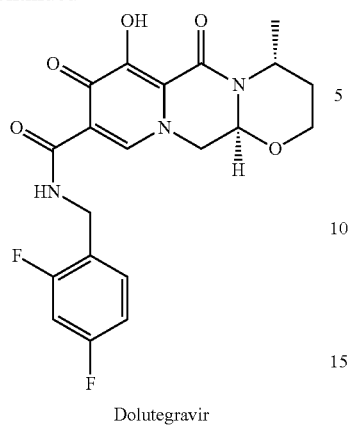

Dolutegravir

According to the '385 patent also described a process for the methyl 3-(benzyloxy)-5-(2,4-difluorobenzylcarbamoyl)-4-oxo-1-(2-oxoethyl)-1,4-dihydropyiridine-2-carboxylate. The synthetic procedure is illustrated in scheme II, below:

Scheme II

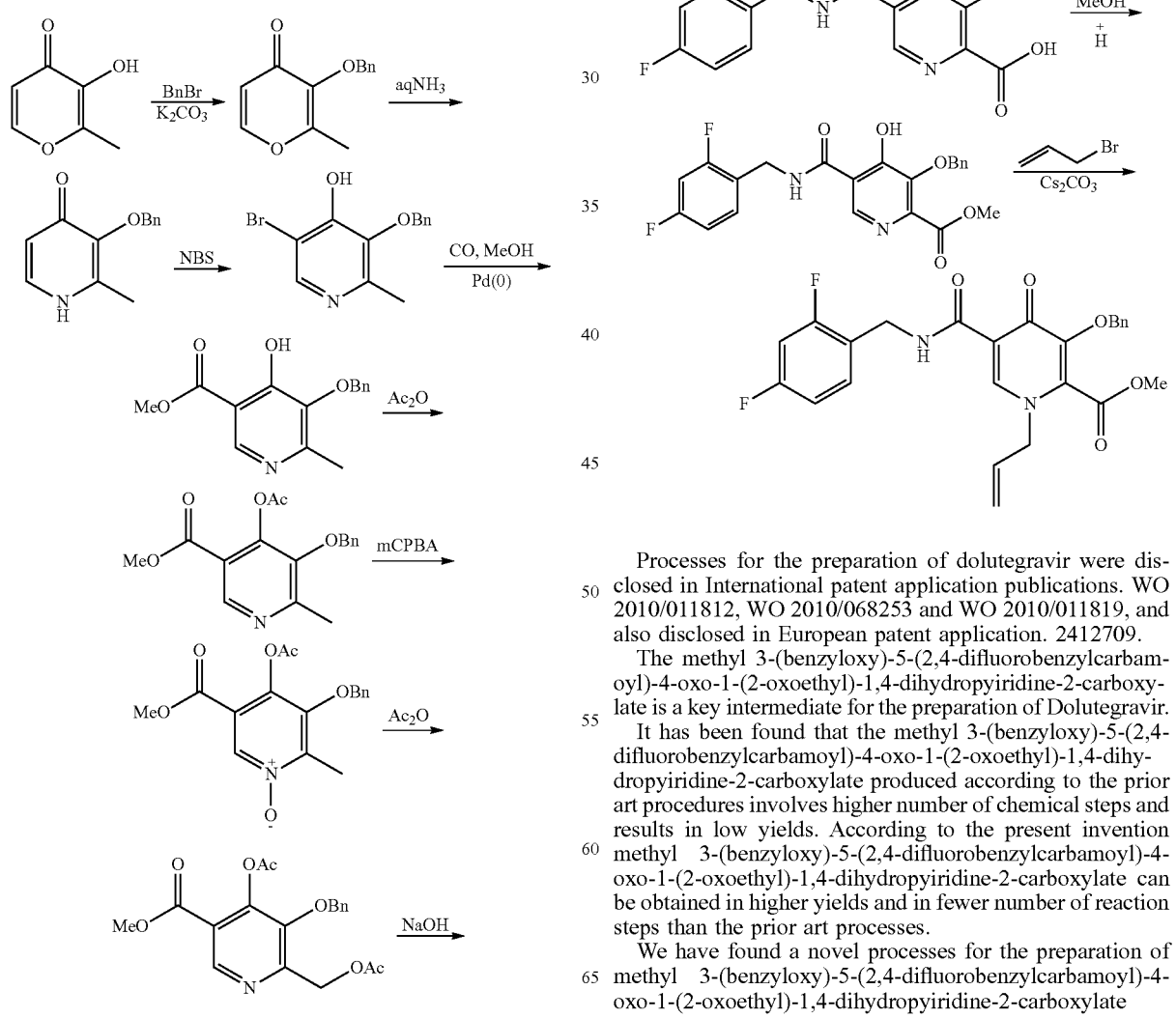

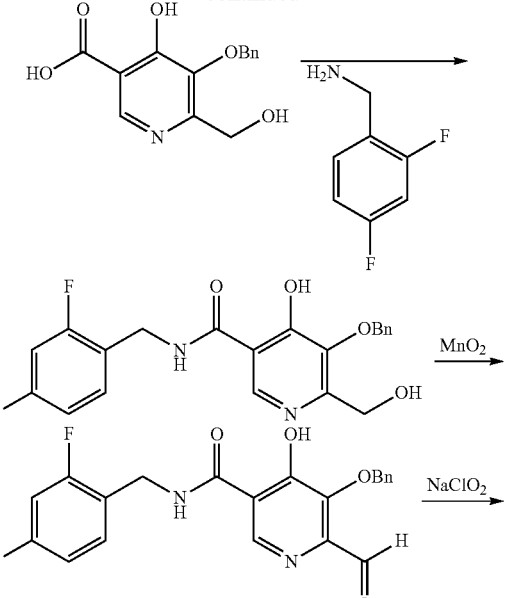

Processes for the preparation of dolutegravir were disclosed in International patent application publications. WO 2010/011812, WO 2010/068253 and WO 2010/011819, and also disclosed in European patent application. 2412709.

The methyl 3-(benzyloxy)-5-(2,4-difluorobenzylcarbamoyl)-4-oxo-1-(2-oxoethyl)-1,4-dihydropyiridine-2-carboxylate is a key intermediate for the preparation of Dolutegravir.

It has been found that the methyl 3-(benzyloxy)-5-(2,4-difluorobenzylcarbamoyl)-4-oxo-1-(2-oxoethyl)-1,4-dihydropyiridine-2-carboxylate produced according to the prior art procedures involves higher number of chemical steps and results in low yields. According to the present invention methyl 3-(benzyloxy)-5-(2,4-difluorobenzylcarbamoyl)-4-oxo-1-(2-oxoethyl)-1,4-dihydropyiridine-2-carboxylate can be obtained in higher yields and in fewer number of reaction steps than the prior art processes.

We have found a novel processes for the preparation of methyl 3-(benzyloxy)-5-(2,4-difluorobenzylcarbamoyl)-4-oxo-1-(2-oxoethyl)-1,4-dihydropyiridine-2-carboxylate using novel intermediate.

The processes of present invention are simple, inexpensive and reproducible and are well suited on an industrial scale.

Thus, an object of the present invention is to provide a novel processes for preparing methyl 3-(benzyloxy)-5-(2,4-difluorobenzylcarbamoyl)-4-oxo-1-(2-oxoethyl)-1,4-dihydropyiridine-2-carboxylate using novel intermediate.

SUMMARY OF THE INVENTION

In one aspect, the present invention provides a novel process for the preparation of methyl 3-(benzyloxy)-5-(2,4-difluorobenzylcarbamoyl)-4-oxo-1-(2-oxoethyl)-1,4-dihydropyiridine-2-carboxylate of formula II, which comprises:
- a) treating the 3-(benzyloxy)-4-oxo-4H-pyran-2-carbaldehyde with trimethyl orthoformate in the presence of camphorsulfonic acid and a suitable solvent to give 3-(benzyloxy)-2-(dimethoxymethyl)-4H-pyran-4-one of formula III;
- b) reacting the 3-(benzyloxy)-2-(dimethoxymethyl)-4H-pyran-4-one obtained in step (a) with methanolic ammonia in the presence of an alcoholic solvent to give 3-(benzyloxy)-2-(dimethoxymethyl)pyridin-4(1H)-one of formula IV;
- c) bromonating the 3-(benzyloxy)-2-(dimethoxymethyl)pyridin-4(1H)-one obtained in step (b) with N-bromosuccinimide in the presence of a chlorinated solvent to give 3-(benzyloxy)-5-bromo-2-(dimethoxymethyl)pyridin-4(1H)-one of formula V;
- d) treating the 3-(benzyloxy)-5-bromo-2-(dimethoxymethyl)pyridin-4(1H)-one obtained in step (c) with n-butyllithium in the presence of dimethylformamide and an ether solvent to give 5-(benzyloxy)-6-(dimethoxymethyl)-4-oxo-1,4-dihydropyridine-3-carbaldehyde of formula VI;
- e) reacting the 5-(benzyloxy)-6-(dimethoxymethyl)-4-oxo-1,4-dihydropyridine-3-carbaldehyde obtained in step (d) with sulfamic acid and sodium chlorite in a suitable solvent to give 5-(benzyloxy)-6-(dimethoxymethyl)-4-oxo-1,4-dihydropyridine-3-carboxylic acid of formula VII;
- f) condensing the 5-(benzyloxy)-6-(dimethoxymethyl)-4-oxo-1,4-dihydropyridine-3-carboxylic acid obtained in step (e) with 2,4-difluorobenzylamine in the presence of 1-(3-dimethylaminopropyl)-3-ethylcarbodiimide hydrochloride, hydroxybenzotriazole and tertiary amine in a suitable solvent to give 5-(benzyloxy)-N-(2,4-difluorobenzyl)-6-(dimethoxymethyl)-4-oxo-1,4-dihydropyridine-3-carboxamide of formula VIII;
- g) condensing the 5-(benzyloxy)-N-(2,4-difluorobenzyl)-6-(dimethoxymethyl)-4-oxo-1,4-dihydropyridine-3-carboxamide obtained in step (f) with allyl bromide in the presence of a base and dimethylformamide to give 1-allyl-5-(benzyloxy)-N-(2,4-difluorobenzyl)-6-(dimethoxymethyl)-4-oxo-1,4-dihydropyridine-3-carboxamide of formula XI;
- h) treating the 1-allyl-5-(benzyloxy)-N-(2,4-difluorobenzyl)-6-(dimethoxymethyl)-4-oxo-1,4-dihydropyridine-3-carboxamide obtained in step (g) with formic acid in a ketonic solvent to give 1-allyl-5-(benzyloxy)-N-(2,4-difluorobenzyl)-6-formyl-4-oxo-1,4-dihydropyridine-3-carboxamide of formula XII;
- i) reacting the 1-allyl-5-(benzyloxy)-N-(2,4-difluorobenzyl)-6-formyl-4-oxo-1,4-dihydropyridine-3-carboxamide obtained in step (h) with sulfamic acid and sodium chlorite in a suitable solvent to give 1-allyl-3-(benzyloxy)-5-(2,4-difluorobenzylcarbamoyl)-4-oxo-1,4-dihydropyridine-2-carboxylic acid of formula XIII; and
- j) methylating the 1-allyl-3-(benzyloxy)-5-(2,4-difluorobenzylcarbamoyl)-4-oxo-1,4-dihydropyridine-2-carboxylic acid with methyl iodide in the presence of a base and dimethylformamide to give methyl 3-(benzyloxy)-5-(2,4-difluorobenzylcarbamoyl)-4-oxo-1-(2-oxoethyl)-1,4-dihydropyridine-2-carboxylate of formula II.

In another aspect, the present invention provides a novel process for the preparation of methyl 3-(benzyloxy)-5-(2,4-difluorobenzylcarbamoyl)-4-oxo-1-(2-oxoethyl)-1,4-dihydropyiridine-2-carboxylate of formula II, which comprises:
- a) treating the 3-(benzyloxy)-4-oxo-4H-pyran-2-carbaldehyde with trimethyl orthoformate in the presence of camphorsulfonic acid and a suitable solvent to give 3-(benzyloxy)-2-(dimethoxymethyl)-4H-pyran-4-one of formula III;
- b) reacting the 3-(benzyloxy)-2-(dimethoxymethyl)-4H-pyran-4-one obtained in step (a) with methanolic ammonia in the presence of an alcoholic solvent to give 3-(benzyloxy)-2-(dimethoxymethyl)pyridin-4(1H)-one of formula IV;
- c) bromonating the 3-(benzyloxy)-2-(dimethoxymethyl)pyridin-4(1H)-one obtained in step (b) with N-bromosuccinimide in the presence of a chlorinated solvent to give 3-(benzyloxy)-5-bromo-2-(dimethoxymethyl)pyridin-4(1H)-one of formula V;
- d) treating the 3-(benzyloxy)-5-bromo-2-(dimethoxymethyl)pyridin-4(1H)-one obtained in step (c) with n-butyllithium in the presence of dimethylformamide and an ether solvent to give 5-(benzyloxy)-6-(dimethoxymethyl)-4-oxo-1,4-dihydropyridine-3-carbaldehyde Formula VI;
- e) condensing the 5-(benzyloxy)-6-(dimethoxymethyl)-4-oxo-1,4-dihydropyridine-3-carbaldehyde obtained in step (d) with allyl bromide in the presence of a base and dimethylformamide to give 1-allyl-5-(benzyloxy)-6-(dimethoxymethyl)-4-oxo-1,4-dihydropyridine-3-carbaldehyde of formula IX;
- f) reacting the 1-allyl-5-(benzyloxy)-6-(dimethoxymethyl)-4-oxo-1,4-dihydropyridine-3-carbaldehyde obtained in step (e) with sulfamic acid and sodium chlorite in a suitable solvent to give 1-allyl-5-(benzyloxy)-6-(dimethoxymethyl)-4-oxo-1,4-dihydropyridine-3-carboxylic acid of formula X;
- g) condensing the 1-allyl-5-(benzyloxy)-6-(dimethoxymethyl)-4-oxo-1,4-dihydropyridine-3-carboxylic acid obtained in step (f) with 2,4-difluorobenzylamine in the presence of 1-(3-dimethylaminopropyl)-3-ethylcarbodiimide hydrochloride, hydroxybenzotriazole and tertiary amine in a suitable solvent to give 1-allyl-5-(benzyloxy)-N-(2,4-difluorobenzyl)-6-(dimethoxymethyl)-4-oxo-1,4-dihydropyridine-3-carboxamide of formula XI;
- h) treating the 1-allyl-5-(benzyloxy)-N-(2,4-difluorobenzyl)-6-(dimethoxymethyl)-4-oxo-1,4-dihydropyridine-3-carboxamide obtained in step (g) with formic acid in a ketonic solvent to give 1-allyl-5-(benzyloxy)-N-(2,4-difluorobenzyl)-6-formyl-4-oxo-1,4-dihydropyridine-3-carboxamide of formula XII;
- i) reacting the 1-allyl-5-(benzyloxy)-N-(2,4-difluorobenzyl)-6-formyl-4-oxo-1,4-dihydropyridine-3-carboxamide obtained in step (h) with sulfamic acid and sodium chlorite in a suitable solvent to give 1-allyl-3-(benzyloxy)-5-(2,4-difluorobenzylcarbamoyl)-4-oxo-1,4-dihydropyridine-2-carboxylic acid of formula XIII; and j) methylating the 1-allyl-3-(benzyloxy)-5-(2,4-difluorobenzylcarbamoyl)-4-oxo-1,4-dihydropyridine-2-carboxylic acid with methyl iodide in the presence of a base and dimethylformamide to give methyl 3-(benzyloxy)-5-(2,4-difluorobenzylcarbamoyl)-4-oxo-1-(2-oxoethyl)-1,4-dihydropyridine-2-carboxylate of formula II.

In another aspect, the present invention provides a novel compound of 3-(benzyloxy)-2-(dimethoxymethyl)-4H-pyran-4-one of formula III:

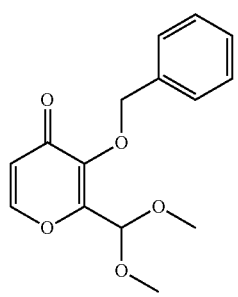

III

In another aspect, the present invention provides a novel compound of 3-(benzyloxy)-2-(dimethoxymethyl)pyridin-4(1H)-one of formula IV:

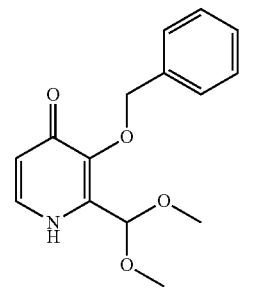

IV

In another aspect, the present invention provides a novel compound of 3-(benzyloxy)-5-bromo-2-(dimethoxymethyl)pyridin-4(1H)-one of formula V:

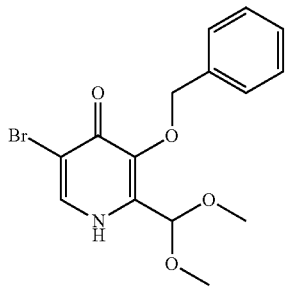

V

In another aspect, the present invention provides a novel compound of 5-(benzyloxy)-6-(dimethoxymethyl)-4-oxo-1,4-dihydropyridine-3-carbaldehyde of formula VI:

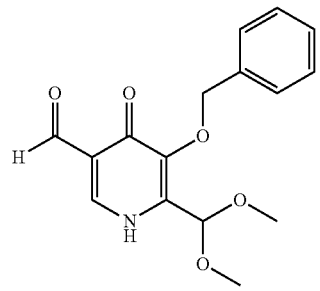

VI

In another aspect, the present invention provides a novel compound of 5-(benzyloxy)-6-(dimethoxymethyl)-4-oxo-1,4-dihydropyridine-3-carboxylic acid of formula VII:

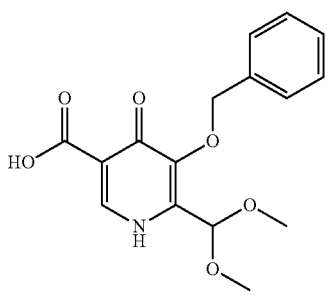

VII

In another aspect, the present invention provides a novel compound of 5-(benzyloxy)-N-(2,4-difluorobenzyl)-6-(dimethoxymethyl)-4-oxo-1,4-dihydropyridine-3-carboxamide of formula VIII:

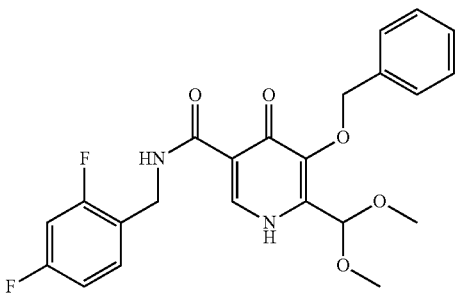

VIII

In another aspect, the present invention provides a novel compound of 1-allyl-5-(benzyloxy)-6-(dimethoxymethyl)-4-oxo-1,4-dihydropyridine-3-carbaldehyde of formula IX:

IX

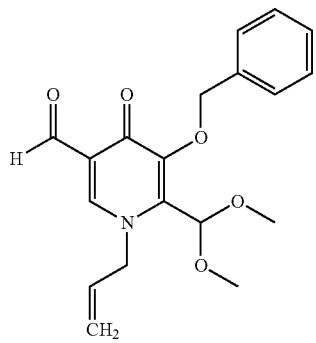

In another aspect, the present invention provides a novel compound of 1-allyl-5-(benzyloxy)-6-(dimethoxymethyl)-4-oxo-1,4-dihydropyridine-3-carboxylic acid of formula X:

X

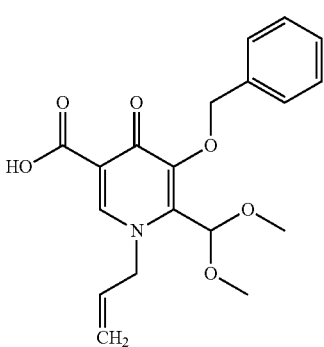

In another aspect, the present invention provides a novel compound of 1-allyl-5-(benzyloxy)-N-(2,4-difluorobenzyl)-6-(dimethoxymethyl)-4-oxo-1,4-dihydropyridine-3-carboxamide of formula XI:

XI

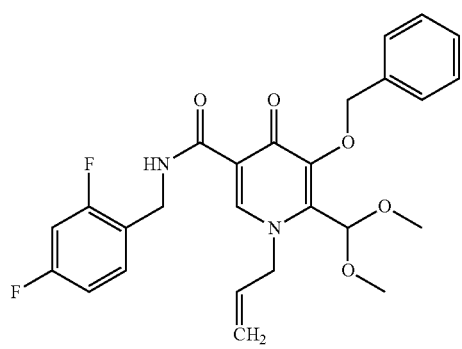

In another aspect, the present invention provides a novel compound of 1-allyl-5-(benzyloxy)-N-(2,4-difluorobenzyl)-6-formyl-4-oxo-1,4-dihydropyridine-3-carboxamide of formula XII:

XII

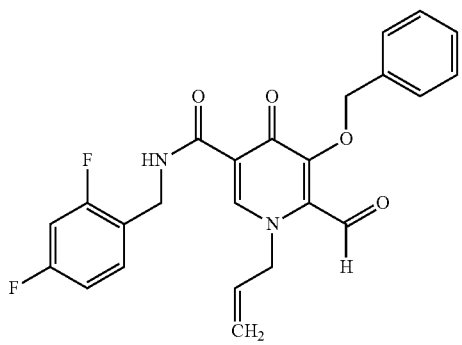 [SMILES: C=CCn1cc(C(=O)NCc2ccc(F)cc2F)c(=O)c(OCc2ccccc2)c1C(=O)OC]

In another aspect, the present invention provides a novel compound of 1-allyl-3-(benzyloxy)-5-(2,4-difluorobenzylcarbamoyl)-4-oxo-1,4-dihydropyridine-2-carboxylic acid of formula XIII:

XIII

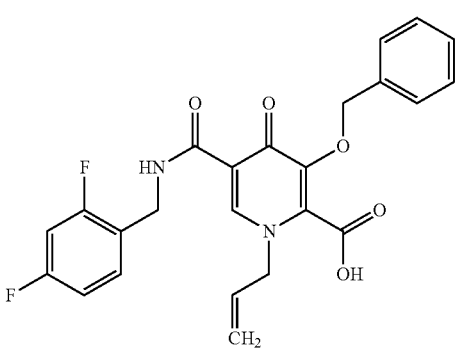

DETAILED DESCRIPTION OF THE INVENTION

As used herein the term "room temperature" refers to a temperature of about 25° C. to about 35° C.

According to one aspect of the present invention, there is provided a novel process for the preparation of methyl 3-(benzyloxy)-5-(2,4-difluorobenzylcarbamoyl)-4-oxo-1-(2-oxoethyl)-1,4-dihydropyiridine-2-carboxylate of formula II, which comprises:

a) treating the 3-(benzyloxy)-4-oxo-4H-pyran-2-carbaldehyde with trimethyl orthoformate in the presence of camphorsulfonic acid and a suitable solvent to give 3-(benzyloxy)-2-(dimethoxymethyl)-4H-pyran-4-one of formula III;

b) reacting the 3-(benzyloxy)-2-(dimethoxymethyl)-4H-pyran-4-one obtained in step (a) with methanolic ammonia in the presence of an alcoholic solvent to give 3-(benzyloxy)-2-(dimethoxymethyl)pyridin-4(1H)-one of formula IV;

c) bromonating the 3-(benzyloxy)-2-(dimethoxymethyl)pyridin-4(1H)-one obtained in step (b) with N-bromosuccinimide in the presence of a chlorinated solvent to give 3-(benzyloxy)-5-bromo-2-(dimethoxymethyl)pyridin-4(1H)-one of formula V;

d) treating the 3-(benzyloxy)-5-bromo-2-(dimethoxymethyl)pyridin-4(1H)-one obtained in step (c) with n-butyllithium in the presence of dimethylformamide and an ether solvent to give 5-(benzyloxy)-6-(dimethoxymethyl)-4-oxo-1,4-dihydropyridine-3-carbaldehyde of formula VI;

e) reacting the 5-(benzyloxy)-6-(dimethoxymethyl)-4-oxo-1,4-dihydropyridine-3-carbaldehyde obtained in step (d) with sulfamic acid and sodium chlorite in a suitable solvent to give 5-(benzyloxy)-6-(dimethoxymethyl)-4-oxo-1,4-dihydropyridine-3-carboxylic acid of formula VII;

f) condensing the 5-(benzyloxy)-6-(dimethoxymethyl)-4-oxo-1,4-dihydropyridine-3-carboxylic acid obtained in step (e) with 2,4-difluorobenzylamine in the presence of 1-(3-dimethylaminopropyl)-3-ethylcarbodiimide hydrochloride, hydroxybenzotriazole and tertiary amine in a suitable solvent to give 5-(benzyloxy)-N-(2,4-difluorobenzyl)-6-(dimethoxymethyl)-4-oxo-1,4-dihydropyridine-3-carboxamide of formula VIII;

g) condensing the 5-(benzyloxy)-N-(2,4-difluorobenzyl)-6-(dimethoxymethyl)-4-oxo-1,4-dihydropyridine-3-carboxamide obtained in step (f) with allyl bromide in the presence of a base and dimethylformamide to give 1-allyl-5-(benzyloxy)-N-(2,4-difluorobenzyl)-6-(dimethoxymethyl)-4-oxo-1,4-dihydropyridine-3-carboxamide of formula XI;

h) treating the 1-allyl-5-(benzyloxy)-N-(2,4-difluorobenzyl)-6-(dimethoxymethyl)-4-oxo-1,4-dihydropyridine-3-carboxamide obtained in step (g) with formic acid in a ketonic solvent to give 1-allyl-5-(benzyloxy)-N-(2,4-difluorobenzyl)-6-formyl-4-oxo-1,4-dihydropyridine-3-carboxamide of formula XII;

i) reacting the 1-allyl-5-(benzyloxy)-N-(2,4-difluorobenzyl)-6-formyl-4-oxo-1,4-dihydropyridine-3-carboxamide obtained in step (h) with sulfamic acid and sodium chlorite in a suitable solvent to give 1-allyl-3-(benzyloxy)-5-(2,4-difluorobenzylcarbamoyl)-4-oxo-1,4-dihydropyridine-2-carboxylic acid of formula XIII; and j) methylating the 1-allyl-3-(benzyloxy)-5-(2,4-difluorobenzylcarbamoyl)-4-oxo-1,4-dihydropyridine-2-carboxylic acid with methyl iodide in the presence of a base and dimethylformamide to give methyl 3-(benzyloxy)-5-(2,4-difluorobenzylcarbamoyl)-4-oxo-1-(2-oxoethyl)-1,4-dihydropyridine-2-carboxylate of formula II.

The suitable solvent used in step (a) may preferably be a solvent or a mixture of solvents selected from methylene chloride, ethylene dichloride, chloroform, carbon tetrachloride, ethyl acetate, methyl acetate, isopropyl acetate, tert-butyl acetate, ethyl formate, methyl formate, methanol, ethanol, isopropanol, tert-butyl alcohol, n-butanol and isobutyl alcohol. More preferably the suitable solvents are methylene chloride and methanol.

Preferably the alcoholic solvent used in step (b) may be a solvent or a mixture of solvents selected from methanol, ethanol, isopropanol, tert-butyl alcohol, n-butanol and isobutyl alcohol, and more preferably the alcoholic solvent is methanol.

The chlorinated solvent used in step (c) may preferably be a solvent or a mixture of solvents selected from methylene chloride, ethylene dichloride, chloroform and carbon tetrachloride, and more preferably the chlorinated solvent is methylene chloride.

Preferably the ether solvent used in step (d) may preferably be a solvent or a mixture of solvents selected from tetrahydrofuran, diethyl ether, diisopropyl ether and tert-butyl methyl ether. More preferably the ether solvent is tetrahydrofuran.

The suitable solvent used in step (e) may preferably be a solvent or a mixture of solvents selected from water, acetone, diethyl ketone, methyl ethyl ketone, methyl propyl ketone, methyl isobutyl ketone, methyl tert-butyl ketone, methylene chloride, ethylene dichloride, chloroform, carbon tetrachloride, ethyl acetate, methyl acetate, isopropyl acetate, tert-butyl acetate, ethyl formate, methyl formate, methanol, ethanol, isopropanol, tert-butyl alcohol, n-butanol and isobutyl alcohol. More preferably the suitable solvents are water, acetone and methanol.

Preferably the suitable solvent used in step (f) may preferably be a solvent or a mixture of solvents selected from dimethylformamide, dimethyl sulfoxide, dimethylacetamide, acetone, diethyl ketone, methyl ethyl ketone, methyl propyl ketone, methyl isobutyl ketone, methyl tert-butyl ketone, methylene chloride, ethylene dichloride, chloroform, carbon tetrachloride, ethyl acetate, methyl acetate, isopropyl acetate, tert-butyl acetate, ethyl formate, methyl formate, methanol, ethanol, isopropanol, tert-butyl alcohol, n-butanol and isobutyl alcohol. More preferably the suitable solvents are dimethylformamide and dimethyl sulfoxide.

The tertiary amine used in step (f) may preferably be selected from N,N-diisopropylethylamine, triethylamine or trimethylamine, and more preferably the tertiary amine is triethylamine.

The base used in step (g) may preferably be an organic base or an inorganic base. More preferably the base is inorganic base selected from sodium carbonate, sodium hydroxide, sodium bicarbonate, potassium hydroxide, potassium carbonate, potassium bicarbonate, cesium carbonate, cesium bicarbonate, calcium carbonate or calcium bicarbonate. Still more preferably the base is cesium carbonate.

Preferably the ketonic solvent used in step (h) may be a solvent or a mixture of solvents selected from acetone, diethyl ketone, methyl ethyl ketone, methyl propyl ketone, methyl isobutyl ketone and methyl tert-butyl ketone, and more preferably the ketonic solvent is acetone.

The suitable solvent used in step (i) may preferably be a solvent or a mixture of solvents selected from water, acetone, diethyl ketone, methyl ethyl ketone, methyl propyl ketone, methyl isobutyl ketone, methyl tert-butyl ketone, methylene chloride, ethylene dichloride, chloroform, carbon tetrachloride, ethyl acetate, methyl acetate, isopropyl acetate, tert-butyl acetate, ethyl formate, methyl formate, methanol, ethanol, isopropanol, tert-butyl alcohol, n-butanol and isobutyl alcohol. More preferably the suitable solvents are water, acetone and methanol.

Preferably the base used in step (j) may be an organic base or an inorganic base. More preferably the base is inorganic base selected from sodium carbonate, sodium hydroxide, sodium bicarbonate, potassium hydroxide, potassium carbonate, potassium bicarbonate, cesium carbonate, cesium bicarbonate, calcium carbonate or calcium bicarbonate. Still more preferably the base is sodium carbonate or sodium bicarbonate.

According to another aspect of the present invention, there is provided a novel process for the preparation of methyl 3-(benzyloxy)-5-(2,4-difluorobenzylcarbamoyl)-4-oxo-1-(2-oxoethyl)-1,4-dihydropyiridine-2-carboxylate of formula II, which comprises:

a) treating the 3-(benzyloxy)-4-oxo-4H-pyran-2-carbaldehyde with trimethyl orthoformate in the presence of camphorsulfonic acid and a suitable solvent to give 3-(benzyloxy)-2-(dimethoxymethyl)-4H-pyran-4-one of formula III;

b) reacting the 3-(benzyloxy)-2-(dimethoxymethyl)-4H-pyran-4-one obtained in step (a) with methanolic ammonia in the presence of an alcoholic solvent to give 3-(benzyloxy)-2-(dimethoxymethyl)pyridin-4(1H)-one of formula IV;
c) bromonating the 3-(benzyloxy)-2-(dimethoxymethyl)pyridin-4(1H)-one obtained in step (b) with N-bromo-succinimide in the presence of a chlorinated solvent to give 3-(benzyloxy)-5-bromo-2-(dimethoxymethyl)pyridin-4(1H)-one of formula V;
d) treating the 3-(benzyloxy)-5-bromo-2-(dimethoxymethyl)pyridin-4(1H)-one obtained in step (c) with n-butyllithium in the presence of dimethylformamide and an ether solvent to give 5-(benzyloxy)-6-(dimethoxymethyl)-4-oxo-1,4-dihydropyridine-3-carbaldehyde Formula VI;
e) condensing the 5-(benzyloxy)-6-(dimethoxymethyl)-4-oxo-1,4-dihydropyridine-3-carbaldehyde obtained in step (d) with allyl bromide in the presence of a base and dimethylformamide to give 1-allyl-5-(benzyloxy)-6-(dimethoxymethyl)-4-oxo-1,4-dihydropyridine-3-carbaldehyde of formula IX;
f) reacting the 1-allyl-5-(benzyloxy)-6-(dimethoxymethyl)-4-oxo-1,4-dihydropyridine-3-carbaldehyde obtained in step (e) with sulfamic acid and sodium chlorite in a suitable solvent to give 1-allyl-5-(benzyloxy)-6-(dimethoxymethyl)-4-oxo-1,4-dihydropyridine-3-carboxylic acid of formula X;
g) condensing the 1-allyl-5-(benzyloxy)-6-(dimethoxymethyl)-4-oxo-1,4-dihydropyridine-3-carboxylic acid obtained in step (f) with 2,4-difluorobenzylamine in the presence of 1-(3-dimethylaminopropyl)-3-ethylcarbodiimide hydrochloride, hydroxybenzotriazole and tertiary amine in a suitable solvent to give 1-allyl-5-(benzyloxy)-N-(2,4-difluorobenzyl)-6-(dimethoxymethyl)-4-oxo-1,4-dihydropyridine-3-carboxamide of formula XI;
h) treating the 1-allyl-5-(benzyloxy)-N-(2,4-difluorobenzyl)-6-(dimethoxymethyl)-4-oxo-1,4-dihydropyridine-3-carboxamide obtained in step (g) with formic acid in a ketonic solvent to give 1-allyl-5-(benzyloxy)-N-(2,4-difluorobenzyl)-6-formyl-4-oxo-1,4-dihydropyridine-3-carboxamide of formula XII;
i) reacting the 1-allyl-5-(benzyloxy)-N-(2,4-difluorobenzyl)-6-formyl-4-oxo-1,4-dihydropyridine-3-carboxamide obtained in step (h) with sulfamic acid and sodium chlorite in a suitable solvent to give 1-allyl-3-(benzyloxy)-5-(2,4-difluorobenzylcarbamoyl)-4-oxo-1,4-dihydropyridine-2-carboxylic acid of formula XIII; and
j) methylating the 1-allyl-3-(benzyloxy)-5-(2,4-difluorobenzylcarbamoyl)-4-oxo-1,4-dihydropyridine-2-carboxylic acid with methyl iodide in the presence of a base and dimethylformamide to give methyl 3-(benzyloxy)-5-(2,4-difluorobenzylcarbamoyl)-4-oxo-1-(2-oxoethyl)-1,4-dihydropyridine-2-carboxylate of formula II.

The suitable solvent used in step (a) may preferably be a solvent or a mixture of solvents selected from methylene chloride, ethylene dichloride, chloroform, carbon tetrachloride, ethyl acetate, methyl acetate, isopropyl acetate, tert-butyl acetate, ethyl formate, methyl formate, methanol, ethanol, isopropanol, tert-butyl alcohol, n-butanol and isobutyl alcohol. More preferably the suitable solvents are methylene chloride and methanol.

Preferably the alcoholic solvent used in step (b) may be a solvent or a mixture of solvents selected from methanol, ethanol, isopropanol, tert-butyl alcohol, n-butanol and isobutyl alcohol, and more preferably the alcoholic solvent is methanol.

The chlorinated solvent used in step (c) may preferably be a solvent or a mixture of solvents selected from methylene chloride, ethylene dichloride, chloroform and carbon tetrachloride, and more preferably the chlorinated solvent is methylene chloride.

Preferably the ether solvent used in step (d) may preferably be a solvent or a mixture of solvents selected from tetrahydrofuran, diethyl ether, diisopropyl ether and tert-butyl methyl ether. More preferably the ether solvent is tetrahydrofuran.

The base used in step (e) may preferably be an organic base or an inorganic base. More preferably the base is inorganic base selected from sodium carbonate, sodium hydroxide, sodium bicarbonate, potassium hydroxide, potassium carbonate, potassium bicarbonate, cesium carbonate, cesium bicarbonate, calcium carbonate or calcium bicarbonate. Still more preferably the base is cesium carbonate.

The suitable solvent used in step (f) may preferably be a solvent or a mixture of solvents selected from water, acetone, diethyl ketone, methyl ethyl ketone, methyl propyl ketone, methyl isobutyl ketone, methyl tert-butyl ketone, methylene chloride, ethylene dichloride, chloroform, carbon tetrachloride, ethyl acetate, methyl acetate, isopropyl acetate, tert-butyl acetate, ethyl formate, methyl formate, methanol, ethanol, isopropanol, tert-butyl alcohol, n-butanol and isobutyl alcohol. More preferably the suitable solvents are water, acetone and methanol.

Preferably the suitable solvent used in step (g) may preferably be a solvent or a mixture of solvents selected from dimethylformamide, dimethyl sulfoxide, dimethylacetamide, acetone, diethyl ketone, methyl ethyl ketone, methyl propyl ketone, methyl isobutyl ketone, methyl tert-butyl ketone, methylene chloride, ethylene dichloride, chloroform, carbon tetrachloride, ethyl acetate, methyl acetate, isopropyl acetate, tert-butyl acetate, ethyl formate, methyl formate, methanol, ethanol, isopropanol, tert-butyl alcohol, n-butanol and isobutyl alcohol. More preferably the suitable solvents are dimethylformamide and dimethyl sulfoxide.

The tertiary amine used in step (g) may preferably be selected from N,N-diisopropylethylamine, triethylamine or trimethylamine, and more preferably the tertiary amine is triethylamine.

Preferably the ketonic solvent used in step (h) may be a solvent or a mixture of solvents selected from acetone, diethyl ketone, methyl ethyl ketone, methyl propyl ketone, methyl isobutyl ketone and methyl tert-butyl ketone, and more preferably the ketonic solvent is acetone.

The suitable solvent used in step (i) may preferably be a solvent or a mixture of solvents selected from water, acetone, diethyl ketone, methyl ethyl ketone, methyl propyl ketone, methyl isobutyl ketone, methyl tert-butyl ketone, methylene chloride, ethylene dichloride, chloroform, carbon tetrachloride, ethyl acetate, methyl acetate, isopropyl acetate, tert-butyl acetate, ethyl formate, methyl formate, methanol, ethanol, isopropanol, tert-butyl alcohol, n-butanol and isobutyl alcohol. More preferably the suitable solvents are water, acetone and methanol.

Preferably the base used in step (j) may be an organic base or an inorganic base. More preferably the base is inorganic base selected from sodium carbonate, sodium hydroxide, sodium bicarbonate, potassium hydroxide, potassium carbonate, potassium bicarbonate, cesium carbonate, cesium bicarbonate, calcium carbonate or calcium bicarbonate. Still more preferably the base is sodium carbonate or sodium bicarbonate.

As a specific example of the process for the preparation of methyl 3-(benzyloxy)-5-(2,4-difluorobenzylcarbamoyl)-4- oxo-1-(2-oxoethyl)-1,4-dihydropyiridine-2-carboxylate of formula II may be represented by the following scheme 1:
Scheme 1
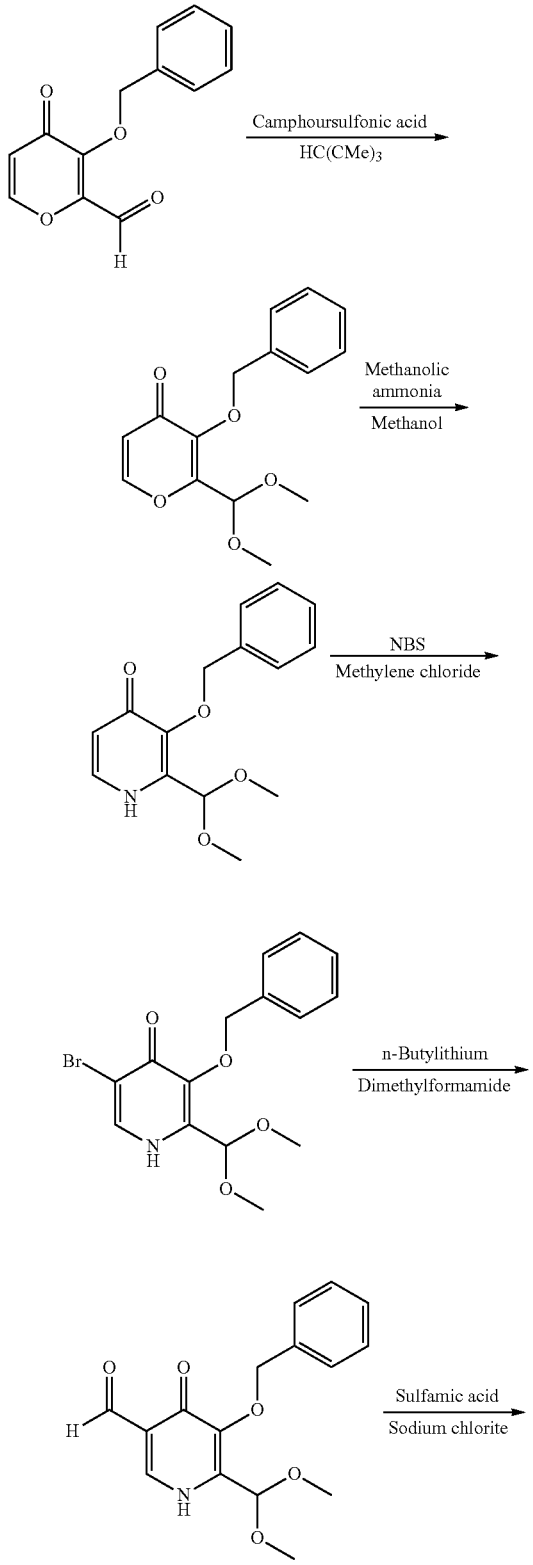
-continued
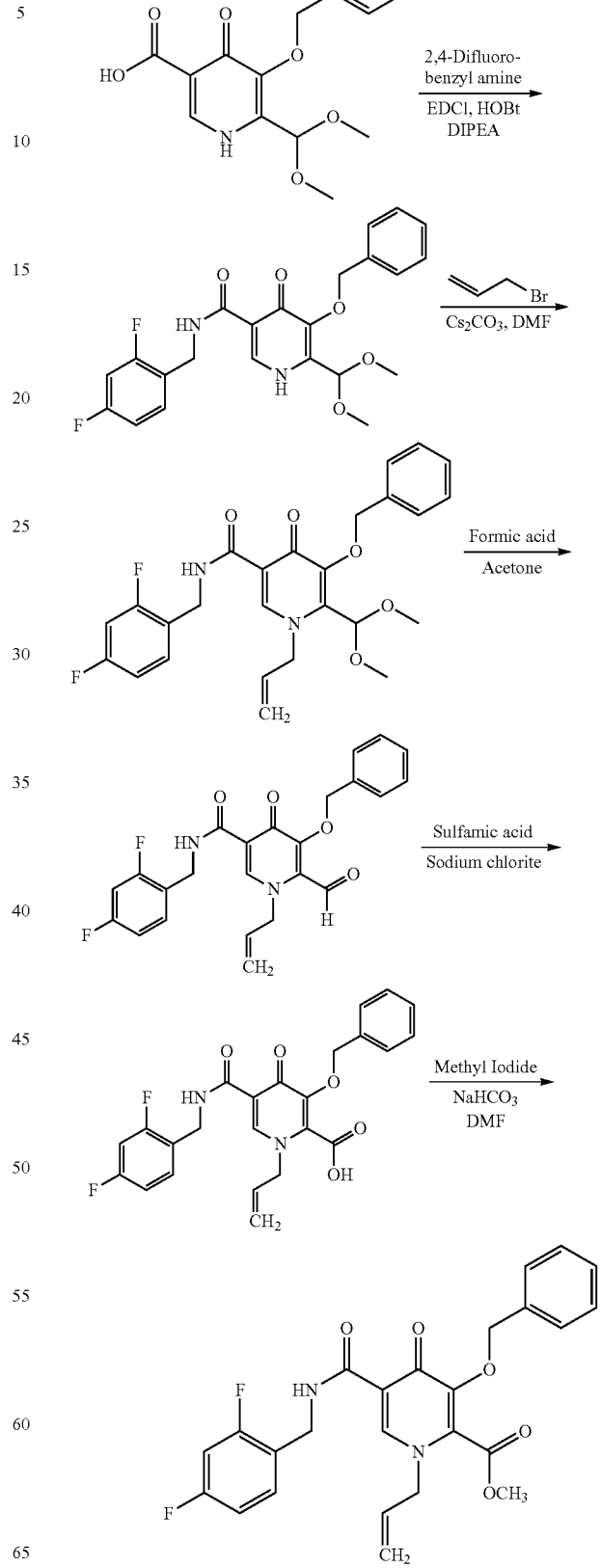

As a specific example of the process for the preparation of methyl 3-(benzyloxy)-5-(2,4-difluorobenzylcarbamoyl)-4-oxo-1-(2-oxoethyl)-1,4-dihydropyiridine-2-carboxylate of formula II may be represented by the following scheme 2:
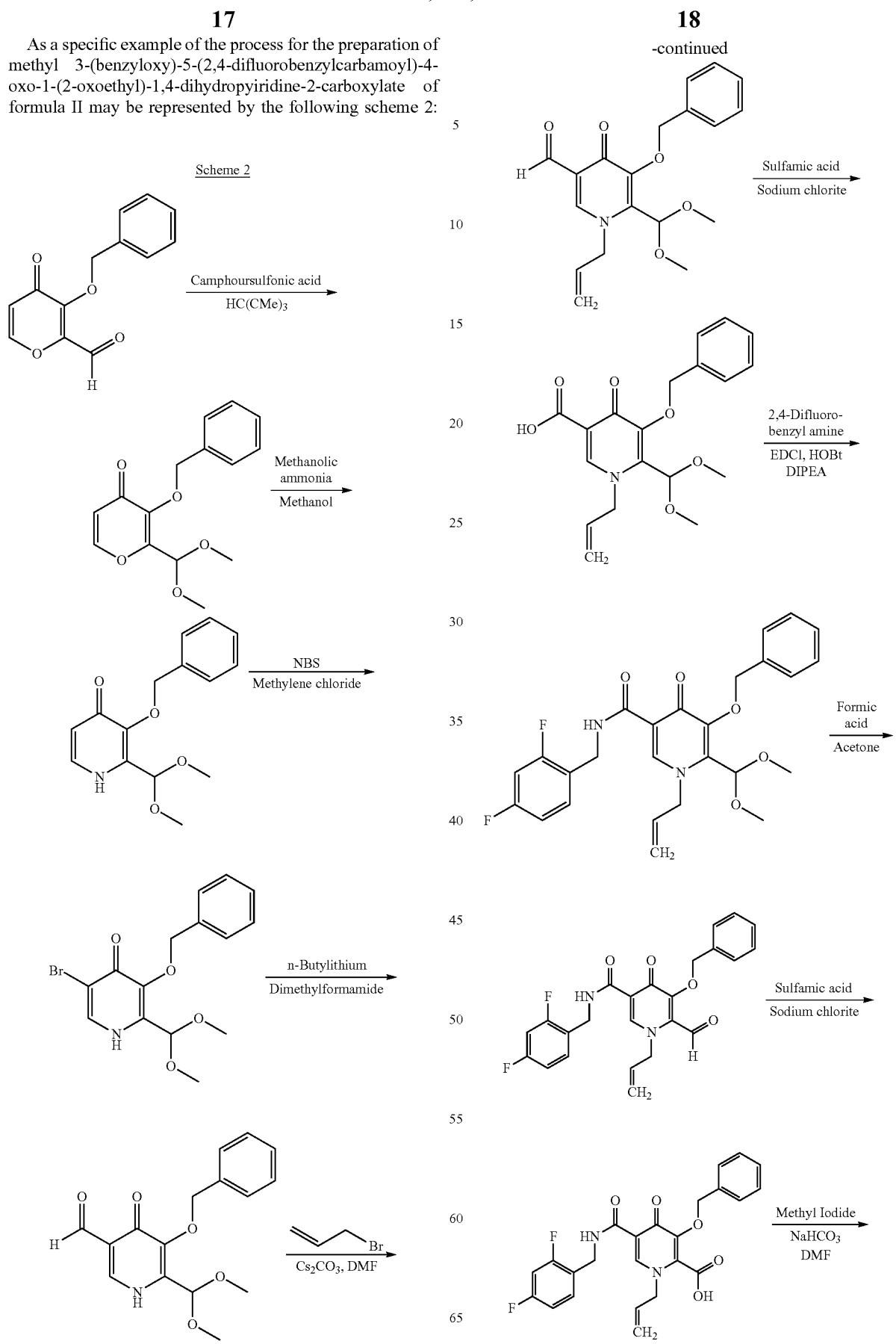

-continued

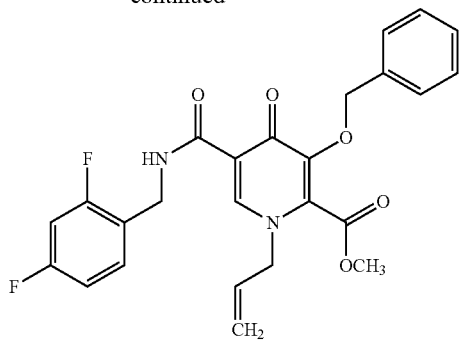

According to another aspect of the present invention, there is provided a novel compound of 3-(benzyloxy)-2-(dimethoxymethyl)-4H-pyran-4-one of formula III:

III

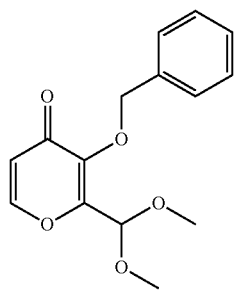

According to another aspect of the present invention, there is provided a novel compound of 3-(benzyloxy)-2-(dimethoxymethyl)pyridin-4(1H)-one of formula IV:

IV

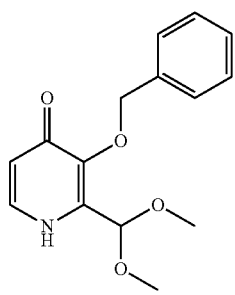

According to another aspect of the present invention, there is provided a novel compound of 3-(benzyloxy)-5-bromo-2-(dimethoxymethyl)pyridin-4(1H)-one of formula V:

V

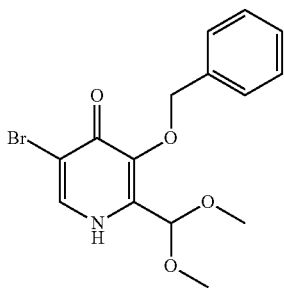

According to another aspect of the present invention, there is provided a novel compound of 5-(benzyloxy)-6-(dimethoxymethyl)-4-oxo-1,4-dihydropyridine-3-carbaldehyde of formula VI:

VI

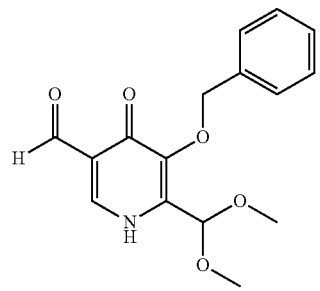

According to another aspect of the present invention, there is provided a novel compound of 5-(benzyloxy)-6-(dimethoxymethyl)-4-oxo-1,4-dihydropyridine-3-carboxylic acid of formula VII:

VII

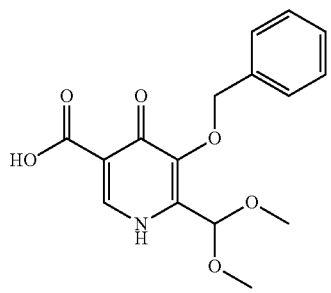

According to another aspect of the present invention, there is provided a novel compound of 5-(benzyloxy)-N-(2,4-difluorobenzyl)-6-(dimethoxymethyl)-4-oxo-1,4-dihydropyridine-3-carboxamide of formula VIII:

VIII

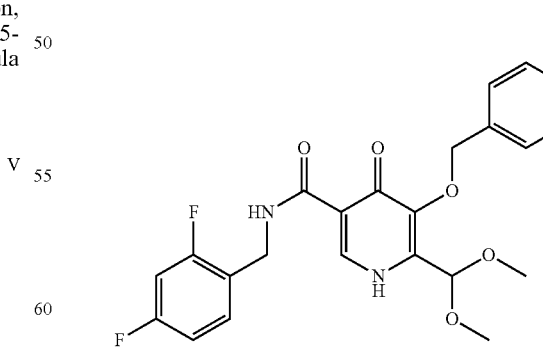

According to another aspect of the present invention, there is provided a novel compound of 1-allyl-5-(benzyloxy)-6-(dimethoxymethyl)-4-oxo-1,4-dihydropyridine-3-carbaldehyde of formula IX:

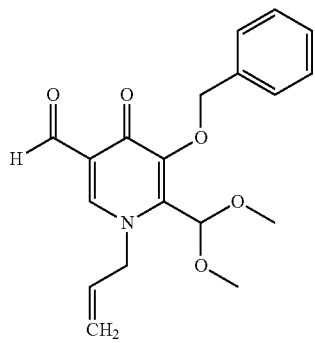

IX

According to another aspect of the present invention, there is provided a novel compound of 1-allyl-5-(benzyloxy)-6-(dimethoxymethyl)-4-oxo-1,4-dihydropyridine-3-carboxylic acid of formula X:

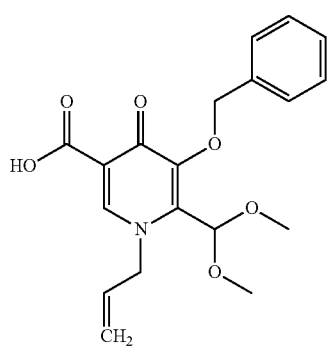

X

According to another aspect of the present invention, there is provided a novel compound of 1-allyl-5-(benzyloxy)-N-(2,4-difluorobenzyl)-6-(dimethoxymethyl)-4-oxo-1,4-dihydropyridine-3-carboxamide of formula XI:

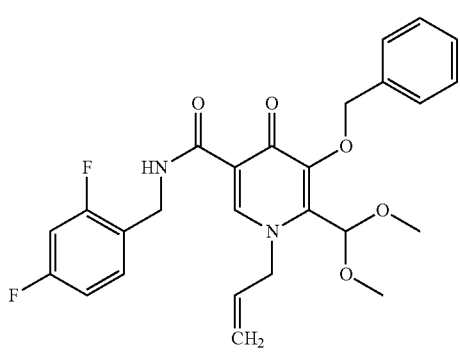

XI

According to another aspect of the present invention, there is provided a novel compound of 1-allyl-5-(benzyloxy)-N-(2,4-difluorobenzyl)-6-formyl-4-oxo-1,4-dihydropyridine-3-carboxamide of formula XII:

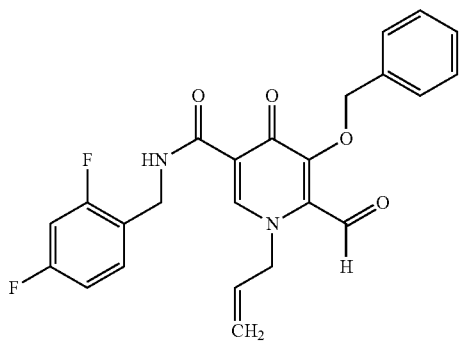

XII

According to another aspect of the present invention, there is provided a novel compound of 1-allyl-3-(benzyloxy)-5-(2,4-difluorobenzylcarbamoyl)-4-oxo-1,4-dihydropyridine-2-carboxylic acid of formula XIII:

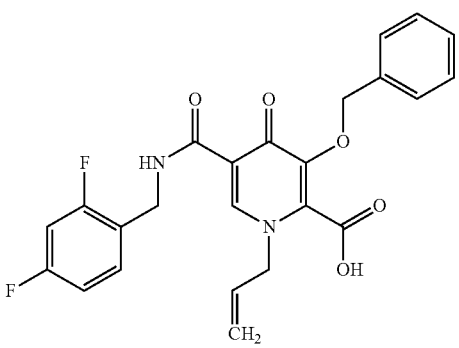 [SMILES: C=CCn1cc(C(=O)NCc2ccc(F)cc2F)c(=O)c(OCc2ccccc2)c1C(=O)OC]

XIII

The invention will now be further described by the following examples, which are illustrative rather than limiting.

EXAMPLES

Example 1

Preparation of 3-(benzyloxy)-2-methyl-4H-pyran-4-one

Maltol (100 gm) was dissolved in acetonitrile (600 ml) and potassium carbonate (153 gm) and benzyl bromide (116 ml) was added to the solution. The contents were heated to 80° C. and stirred for 3 hours. The reaction mass was cooled to room temperature and filtered. The solvent was distilled off from the filtrate thus obtained under reduced pressure to obtain 155 gm of 3-(benzyloxy)-2-methyl-4H-pyran-4-one.

Example 2

Preparation of 3-(benzyloxy)-4-oxo-4H-pyran-2-carbaldehyde

To a 3-(benzyloxy)-2-methyl-4H-pyran-4-one (80 gm) was added bromo benzene (800 ml) and selenium oxide (82 gm) at room temperature. The reaction mixture was heated to 160° C. and stirred for 24 hours. The reaction mass was cooled to room temperature and filtered through celite. The filtrate was concentrated under reduced pressure to obtain 54 gm of 3-(benzyloxy)-4-oxo-4H-pyran-2-carbaldehyde.

Example 3

Preparation of 3-(benzyloxy)-2-(dimethoxymethyl)-4H-pyran-4-One of Formula III 3-(Benzyloxy)-4-oxo-4H-pyran-2-carbaldehyde (54 gm) was dissolved in a mixture of methylene chloride and methanol (1:1; 540 ml). Trimethyl orthoformate (51 ml) and camphorsulfonic acid (11 gm) were added to the solution and the reaction mixture was heated to 60° C. The reaction mass was stirred for 3 hours at 60° C. and the methanol solvent was distilled off, and then diluted with saturated aqueous sodium bicarbonate solution (250 ml) and extracted with methylene chloride. Combined organic layers were dried with anhydrous sodium sulfate and concentrated under reduced pressure to obtain 50 gm of 3-(benzyloxy)-2-(dimethoxymethyl)-4H-pyran-4-one.

$^1$H NMR (300 MHz, CDCl$_3$): δ 7.73 (d, J=5.7 Hz, 1H), 7.39-7.36 (m, 5H), 6.43 (d, J=5.7 Hz, 1H), 5.25 (s, 1H), 5.24 (s, 2H), 3.3 (s, 6H).

Example 4

Preparation of 3-(benzyloxy)-2-(dimethoxymethyl) pyridin-4(1H)-One of Formula IV 3-(Benzyloxy)-2-(dimethoxymethyl)-4H-pyran-4-one (50 gm) was dissolved in methanol (100 ml) and methanolic ammonia solution (250 ml) was then added. The reaction mixture was stirred for 12 hours at room temperature and concentrated under reduced pressure to obtain 32 gm of 3-(benzyloxy)-2-(dimethoxymethyl)pyridin-4(1H)-one.

$^1$H NMR (300 MHz, CDCl$_3$): δ 9.34 (bs, 1H), 7.44-7.3 (m, 6H), 6.5 (d, J=6.9 Hz, 1H), 5.28 (bs, 3H), 3.26 (s, 6H).

Example 5

Preparation of 3-(benzyloxy)-5-bromo-2-(dimethoxymethyl)pyridin-4(1H)-One of Formula V To a 3-(benzyloxy)-2-(dimethoxymethyl)pyridin-4(1H)-one (32 gm) was added methylene chloride (320 ml) and N-bromosuccinimide (23 gm) at 0° C. The reaction mixture was stirred for 3 hours at 0° C. to room temperature. The reaction mixture was added water (300 ml) and extracted with methylene chloride. Combined organic layers were dried with anhydrous sodium sulfate and concentrated to obtain a residual solid. The residual solid thus obtained was purified by silica gel column chromatography with a mixture of ethyl acetate and n-hexane (1:2) to obtain 28.5 gm of 3-(benzyloxy)-5-bromo-2-(dimethoxymethyl)pyridin-4(1H)-one.

$^1$H NMR (300 MHz, CDCl$_3$): δ 8.94 (bs, 1H), 7.82 (s, 1H), 7.48-7.45 (m, 2H), 7.39-7.29 (m, 3H), 5.3-5.28 (m, 3H), 3.29 (s, 6H).

Example 6

Preparation of 5-(benzyloxy)-6-(dimethoxymethyl)-4-oxo-1,4-dihydropyridine-3-carbaldehyde of Formula VI To a 3-(benzyloxy)-5-bromo-2-(dimethoxymethyl)pyridin-4(1H)-one (8.5 gm) was added dry tetrahydrofuran (128 ml) and a solution of n-butyllithium in hexane (24 ml in 2.5 molar hexane) slowly at −78° C. under nitrogen atmosphere. The reaction mixture was stirred for 45 minutes at −78° C. and dimethylformamide (3.7 ml) was then added at −78° C. The reaction mixture was stirred for 45 minutes at −78° C. and heated to −10° C. The reaction mass was quenched with aqueous ammonium chloride and extracted with ethyl acetate. Combined organic layers were dried with anhydrous sodium sulfate and concentrated to obtain a residual solid. The residual solid thus obtained was purified by neutral alumina column chromatography with ethyl acetate and n-hexane (1:1) to obtain 4.8 gm of 5-(benzyloxy)-6-(dimethoxymethyl)-4-oxo-1,4-dihydropyridine-3-carbaldehyde.

$^1$H NMR (300 MHz, CDCl$_3$): δ 10.36 (s, 1H), 8.18 (s, 1H), 7.46-7.31 (m, 5H), 5.34 (s, 2H), 5.31 (s, 1H), 3.33 (s, 6H).

Example 7

Preparation of 5-(benzyloxy)-6-(dimethoxymethyl)-4-oxo-1,4-dihydropyridine-3-carboxylic acid of Formula VII 5-(Benzyloxy)-6-(dimethoxymethyl)-4-oxo-1,4-dihydropyridine-3-carbaldehyde (8 gm) was dissolved in a mixture of acetone and water (1:1, 80 ml) at 0° C. To the solution was added sulfamic acid (6.4 gm) and sodium chlorite (4.8 gm) at 0° C. The reaction mixture was stirred for 5 hours at 0° C. to room temperature and the acetone solvent was distilled off, and then diluted with 1N hydrochloric acid and extracted with methylene chloride. Combined organic layers were dried with anhydrous sodium sulfate and concentrated under reduced pressure to obtain 5.8 gm of 5-(benzyloxy)-6-(dimethoxymethyl)-4-oxo-1,4-dihydropyridine-3-carboxylic acid.

$^1$H NMR (300 MHz, CDCl$_3$): δ 15.84 (bs, 1H), 12.86 (bs, 1H), 8.24 (d, J=6.6 Hz, 1H), 7.48-7.33 (m, 5H), 5.45 (s, 1H), 5.22 (s, 2H), 3.29 (s, 6H).

Example 8

Preparation of 5-(benzyloxy)-N-(2,4-difluorobenzyl)-6-(dimethoxymethyl)-4-oxo-1,4-dihydropyridine-3-carboxamide of Formula VIII To 5-(benzyloxy)-6-(dimethoxymethyl)-4-oxo-1,4-dihydropyridine-3-carboxylic acid (4.4 gm) was added dimethylformamide (66 ml), 1-(3-dimethylaminopropyl)-3-ethylcarbodiimide hydrochloride (4 gm) and hydroxybenzotriazole (1.8 gm) sequentially at 0° C. under nitrogen atmosphere. To the reaction mixture was added triethylamine (7.7 ml) and 2,4-difluorobenzylamine (2.2 ml) at 0° C. and stirred for 48 hours at room temperature. The reaction mixture was diluted with water (50 ml) and then extracted with methylene chloride. Combined organic layers were dried with anhydrous sodium sulfate and concentrated to obtain a residual solid. The residual solid was purified by silica gel column chromatography with a mixture of ethyl acetate and n-hexane (2:3) to obtain 3.5 gm of 5-(benzyloxy)-N-(2,4-difluorobenzyl)-6-(dimethoxymethyl)-4-oxo-1,4-dihydropyridine-3-carboxamide.

$^1$H NMR (300 MHz, CDCl$_3$): δ 10.6 (bs, 1H), 9.23 (bs, 1H), 8.55 (s, 1H), 7.48-7.32 (m, 6H), 6.86-6.77 (m, 2H), 5.31 (s, 1H), 5.28 (s, 2H), 4.66 (d, J=6 Hz, 2H), 3.29 (s, 6H).

Example 9

Preparation of 1-allyl-5-(benzyloxy)-6-(dimethoxymethyl)-4-oxo-1,4-dihydropyridine-3-carbaldehyde of Formula IX 5-(Benzyloxy)-6-(dimethoxymethyl)-4-oxo-1,4-dihydropyridine-3-carbaldehyde (10 gm) was dissolved in dimethylformamide (60 ml) and cesium carbonate (13 gm) and allyl bromide (4.2 ml) were then added. The reaction mixture was heated to 80° C. and stirred for 1 hour. The reaction mass was cooled to room temperature, and then diluted with water (100 ml) and extracted with ethyl acetate. Combined organic layers were dried with anhydrous sodium sulfate and concentrated to obtain 9.6 gm of 1-allyl-5-(benzyloxy)-6-(dimethoxymethyl)-4-oxo-1,4-dihydropyridine-3-carbaldehyde.

$^1$H NMR (300 MHz, CDCl$_3$): δ 10.38 (s, 1H), 7.93 (s, 1H), 7.4-7.29 (m, 5H), 5.93-5.85 (m, 1H), 5.47 (s, 1H), 5.32-5.18 (m, 4H), 4.76-4.63 (m, 2H), 3.21 (s, 6H).

Example 10

Preparation of 1-allyl-5-(benzyloxy)-6-(dimethoxymethyl)-4-oxo-1,4-dihydropyridine-3-carboxylic acid of Formula X 1-Allyl-5-(benzyloxy)-6-(dimethoxymethyl)-4-oxo-1,4-dihydropyridine-3-carbaldehyde (13 gm) was dissolved in a mixture of acetone and water (1:1, 130 ml) at 0° C. To the solution was added sulfamic acid (9.2 gm) and sodium chlorite (6.8 gm) at 0° C. The reaction mixture was stirred for 3 hours at 0° C. to room temperature and the acetone solvent was distilled off, and then diluted with 1N hydrochloric acid and extracted with ethyl acetate. Combined organic layers were dried with anhydrous sodium sulfate and concentrated under reduced pressure to obtain 5.5 gm of 1-allyl-5-(benzyloxy)-6-(dimethoxymethyl)-4-oxo-1,4-dihydropyridine-3-carboxylic acid.

$^1$H NMR (300 MHz, CDCl$_3$): δ 15.42 (bs, 1H), 8.38 (s, 1H), 7.42-7.28 (m, 5H), 5.91-5.85 (m, 1H), 5.55 (s, 1H), 5.36-5.22 (m, 4H), 4.85 (d, J=6.0 Hz, 2H), 3.27 (s, 6H).

Example 11

Preparation of 1-allyl-5-(benzyloxy)-N-(2,4-difluorobenzyl)-6-(dimethoxymethyl)-4-oxo-1,4-dihydropyridine-3-carboxamide of Formula XI 5-(Benzyloxy)-N-(2,4-difluorobenzyl)-6-(dimethoxymethyl)-4-oxo-1,4-dihydropyridine-3-carboxamide (1.4 gm) as obtained in example 8 was dissolved in dimethylformamide (8 ml) and cesium carbonate (1.2 gm) and allyl bromide (0.4 ml) were then added. The reaction mixture was heated to 80° C. and stirred for 1 hour. The reaction mass was cooled to room temperature, and then diluted with water (20 ml) and extracted with ethyl acetate. Combined organic layers were dried with anhydrous sodium sulfate and concentrated to obtain 1.1 gm of 1-allyl-5-(benzyloxy)-N-(2,4-difluorobenzyl)-6-(dimethoxymethyl)-4-oxo-1,4-dihydropyridine-3-carboxamide.

$^1$H NMR (300 MHz, CDCl$_3$): δ 10.6 (bs, 1H), 8.42 (s, 1H), 7.41-7.36 (m, 6H), 6.83-6.79 (m, 2H), 5.9-5.88 (m, 1H), 5.51 (s, 1H), 5.28-5.19 (m, 4H), 4.84-4.7 (m, 2H), 4.64 (d, J=6.0 Hz, 2H), 3.24 (s, 6H).

Example 12

Preparation of 1-allyl-5-(benzyloxy)-N-(2,4-difluorobenzyl)-6-(dimethoxymethyl)-4-oxo-1,4-dihydropyridine-3-carboxamide of Formula XI To a 1-allyl-5-(benzyloxy)-6-(dimethoxymethyl)-4-oxo-1,4-dihydropyridine-3-carboxylic acid (5.5 gm) as obtained in example 10 was added dimethylformamide (33 ml), 1-(3-dimethylaminopropyl)-3-ethylcarbodiimide hydrochloride (4.4 gm) and hydroxybenzotriazole (2.1 gm) sequentially at 0° C. under nitrogen atmosphere. Triethylamine (8.6 ml) and 2,4-difluorobenzylamine (2.2 ml) were added to the reaction mixture and stirred for 48 hours at room temperature. The reaction mixture was diluted with water (50 ml) and extracted with methylene chloride. Combined organic layers were dried with anhydrous sodium sulfate and concentrated to obtain a residual solid. The residual solid was purified by silica gel column chromatography with a mixture of ethyl acetate and n-hexane (2:3) to obtain 2 gm of 1-allyl-5-(benzyloxy)-N-(2,4-difluorobenzyl)-6-(dimethoxymethyl)-4-oxo-1,4-dihydropyridine-3-carboxamide.

Example 13

Preparation of 1-allyl-5-(benzyloxy)-N-(2,4-difluorobenzyl)-6-formyl-4-oxo-1,4-dihydropyridine-3-carboxamide of Formula XII 1-Allyl-5-(benzyloxy)-N-(2,4-difluorobenzyl)-6-(dimethoxymethyl)-4-oxo-1,4-dihydropyridine-3-carboxamide (1.1 gm) was dissolved in acetone (4.4 ml) and added formic acid (98%; 4.4 ml) at room temperature. The reaction mixture was heated to 80° C. and stirred for 3 hours. The reaction mixture was quenched with saturated aqueous sodium bicarbonate solution at 0° C. and extracted with ethyl acetate. Combined organic layers were dried with anhydrous sodium sulfate and concentrated under reduced pressure to obtain 0.9 gm of 1-allyl-5-(benzyloxy)-N-(2,4-difluorobenzyl)-6-formyl-4-oxo-1,4-dihydropyridine-3-carboxamide.

$^1$H NMR (300 MHz, CDCl$_3$): δ 10.34 (bs, 1H), 9.96 (s, 1H), 8.41 (s, 1H), 7.42-7.32 (m, 6H), 6.88-6.79 (m, 2H), 5.87-5.78 (m, 1H), 5.5 (s, 2H), 5.19 (d, J=10.5 Hz, 1H), 4.96-4.85 (m, 3H), 4.66 (d, J=5.7 Hz, 2H).

Example 14

Preparation of 1-allyl-3-(benzyloxy)-5-(2,4-difluorobenzylcarbamoyl)-4-oxo-1,4-dihydropyridine-2-carboxylic acid of Formula XIII 1-Allyl-5-(benzyloxy)-N-(2,4-difluorobenzyl)-6-formyl-4-oxo-1,4-dihydropyridine-3-carboxamide (0.9 gm) was dissolved in a mixture of acetone and water (1:1; 9 ml) at 0° C. To the solution was added sulfamic acid (0.49 gm) and sodium chlorite (0.37 gm) at 0° C. The reaction mixture was stirred for 3 hours at 0° C. to room temperature and the acetone solvent was distilled off, and then diluted with 1N hydrochloric acid and extracted with ethyl acetate. Combined organic layers were dried with anhydrous sodium sulfate and concentrated under reduced pressure to obtain 0.8 gm of 1-allyl-3-(benzyloxy)-5-(2,4-difluorobenzylcarbamoyl)-4-oxo-1,4-dihydropyridine-2-carboxylic acid.

$^1$H NMR (300 MHz, DMSO): δ 10.43 (t, J=5.7 Hz, 1H), 8.54 (s, 1H), 7.47-7.23 (m, 7H), 7.11-7.06 (m, 1H), 6.02-

5.93 (m, 1H), 5.3 (d, J=9.9 Hz, 1H), 5.24-5.09 (m, 3H), 4.75 (d, J=5.4 Hz, 2H), 4.55 (d, J=5.7 Hz, 2H).

Example 15

Preparation of methyl 3-(benzyloxy)-5-(2,4-difluorobenzylcarbamoyl)-4-oxo-1-(2-oxoethyl)-1,4-dihydropyridine-2-carboxylate of Formula II To a 1-allyl-3-(benzyloxy)-5-(2,4-difluorobenzylcarbamoyl)-4-oxo-1,4-dihydropyridine-2-carboxylic acid (3 gm) was added N-methylpyrrolidone (15 ml), sodium bicarbonate (1.7 gm) and methyl iodide (0.84 ml) at 0° C. The reaction mixture was allowed to room temperature and stirred for 2 hours. The reaction mixture was acidified with 1N hydrochloric acid and extracted with ethyl acetate. Combined organic layers were dried with anhydrous sodium sulfate and concentrated under reduced pressure to obtain 2 gm of methyl 3-(benzyloxy)-5-(2,4-difluorobenzylcarbamoyl)-4-oxo-1-(2-oxoethyl)-1,4-dihydropyridine-2-carboxylate.

$^1$H NMR (300 MHz, CDCl$_3$): δ 10.44 (t, J=5.7 Hz, 1H), 8.43 (s, 1H), 7.39-7.34 (m, 6H), 6.86-6.77 (m, 2H), 5.93-5.8 (m, 1H), 5.35 (d, J=10.5 Hz, 1H), 5.29-5.19 (m, 3H), 4.64 (d, J=6.0 Hz, 2H), 4.53 (d, J=5.7 Hz, 2H), 3.76 (s, 3H).

Example 16

Preparation of methyl 3-(benzyloxy)-5-(2,4-difluorobenzylcarbamoyl)-1-(2,3-dihydroxypropyl)-4-oxo-1,4-dihydropyridine-2-carboxylate Methyl 3-(benzyloxy)-5-(2,4-difluorobenzylcarbamoyl)-4-oxo-1-(2-oxoethyl)-1,4-dihydropyridine-2-carboxylate (0.7 gm) was dissolved in a mixture acetone and water (9:1, 14 ml) at 0° C. To the solution was added N-methylmorpholine N-oxide (1.05 gm) and a solution 2% osmium tetroxide in toluene (3.8 ml) at 0° C. The reaction mixture was allowed to room temperature and stirred for 5 hours, and then quenched with saturated sodium bisulfite and extracted with ethyl acetate. Combined organic layers were dried with anhydrous sodium sulfate and concentrated under reduced pressure to obtain 0.6 gm of methyl 3-(benzyloxy)-5-(2,4-difluorobenzylcarbamoyl)-1-(2,3-dihydroxypropyl)-4-oxo-1,4-dihydropyridine-2-carboxylate.

$^1$H NMR (300 MHz, CDCl$_3$): δ 10.58 (t, J=5.7 Hz, 1H), 8.48 (s, 1H), 7.42-7.28 (m, 6H), 6.86-6.77 (m, 2H), 5.28-5.19 (m, 2H), 4.63-4.59 (m, 2H), 4.12-3.93 (m, 3H), 3.89 (s, 3H), 3.72-3.63 (m, 1H), 3.58-3.48 (m, 1H).

Example 17

Preparation of methyl 3-(benzyloxy)-5-(2,4-difluorobenzylcarbamoyl)-4-oxo-1-(2-oxoethyl)-1,4-dihydropyridine-2-carboxylate To a methyl 3-(benzyloxy)-5-(2,4-difluorobenzylcarbamoyl)-1-(2,3-dihydroxypropyl)-4-oxo-1,4-dihydropyridine-2-carboxylate (0.6 gm) was added methylene chloride (0.6 gm), saturated sodium bicarbonate (0.6 ml) and sodium periodate (1.28 gm) at 0° C. The reaction mixture was allowed to room temperature and stirred for 14 hours. The reaction mass was filtered through celite bed and then concentrated to obtain 0.5 gm of methyl 3-(benzyloxy)-5-(2,4-difluorobenzylcarbamoyl)-4-oxo-1-(2-oxoethyl)-1,4-dihydropyridine-2-carboxylate.

Example 18

Preparation of (4R,12aS)-7-(benzyloxy)-N-(2,4-difluorobenzyl)-4-methyl-6,8-dioxo-3,4,6,8,12,12a-hexahydro-2H-[1,3]oxazino[3,2-d]pyrido[1,2-a]pyrazine-9-carboxamide Methyl 3-(benzyloxy)-5-(2,4-difluorobenzylcarbamoyl)-4-oxo-1-(2-oxoethyl)-1,4-dihydropyridine-2-carboxylate (0.5 gm) was dissolved in toluene (5 ml) and methanol (0.5 ml). (R)-3-Aminobutane-1-ol (0.17 gm) and acetic acid (0.5 ml) were added to the solution at room temperature. The contents were heated to 120° C. and stirred for 4 hours. The reaction mass was cooled to 0° C., and then quenched with saturated sodium bicarbonate solution and extracted with ethyl acetate. Combined organic layers were dried with anhydrous sodium sulfate and concentrated to obtain a residual solid. The residual solid was purified by silica gel column chromatography with a mixture of ethyl acetate and n-hexane (1:3) to obtain 0.2 gm of (4R,12aS)-7-(benzyloxy)-N-(2,4-difluorobenzyl)-4-methyl-6,8-dioxo-3,4,6,8,12,12a-hexahydro-2H-[1,3]oxazino[3,2-d]pyrido[1,2-a]pyrazine-9-carboxamide.

$^1$H NMR (300 MHz, CDCl$_3$): δ 10.41 (bs, 1H), 8.35 (s, 1H), 7.63-7.61 (m, 2H), 7.38-7.33 (m, 5H), 6.86-6.78 (m, 2H), 5.33-5.25 (m, 2H), 5.17 (t, J=5.7 Hz, 1H), 5.03-4.99 (m, 1H), 4.64 (d, J=5.7 Hz, 2H), 4.25-4.19 (m, 1H), 4.16-4.07 (m, 1H), 3.97-3.95 (m, 2H), 2.29-2.12 (m, 1H), 1.54-1.49 (m, 1H), 1.34 (d, J=7.2 Hz, 3H).

Example 19

Preparation of Dolutegravir (4R,12aS)-7-(Benzyloxy)-N-(2,4-difluorobenzyl)-4-methyl-6,8-dioxo-3,4,6,8,12,12a-hexahydro-2H-[1,3]oxazino[3,2-d]pyrido[1,2-a]pyrazine-9-carboxamide (0.4 gm) was dissolved in a mixture of ethyl acetate and ethanol (10:1, 4.2 ml) and 10% palladium on carbon (0.042 gm) was then added. To the reaction mass was applied hydrogen gas via a balloon for 30 minutes. The resultant reaction mass was filtered through celite bed and concentrated to obtain a residual solid. The residual solid was purified by silica gel column chromatography with a mixture of chloroform and methanol (99:1) to obtain 0.06 gm of dolutegravir.

$^1$H NMR (300 MHz, DMSO): δ 12.5 (s, 1H), 10.35 (t, J=5.7 Hz, 1H), 8.5 (s, 1H), 7.42-7.34 (m, 1H), 7.27-7.21 (m, 1H), 7.1-7.03 (m, 1H), 5.45 (t, J=4.8 Hz, 1H), 4.81-4.77 (m, 1H), 4.6-4.5 (m, 3H), 4.34 (dd, J=5.7, 13.8 Hz, 1H), 4.07-3.99 (m, 1H), 3.9-3.88 (m, 1H), 2.05-1.96 (m, 1H), 1.56-1.52 (m, 1H), 1.33 (d, J=6.9 Hz, 3H).

We claim:

1. A process for the preparation of Dolutegravir of formula I the process comprising:
   a) treating the 3-(benzyloxy)-4-oxo-4H-pyran-2-carbaldehyde with trimethyl orthoformate in the presence of camphorsulfonic acid and a suitable solvent to give 3-(benzyloxy)-2-(dimethoxymethyl)-4H-pyran-4-one of formula III;
   b) reacting the 3-(benzyloxy)-2-(dimethoxymethyl)-4H-pyran-4-one obtained in step (a) with methanolic ammonia in the presence of an alcoholic solvent to give 3-(benzyloxy)-2-(dimethoxymethyl)pyridin-4(1H)-one of formula IV;
   c) brominating the 3-(benzyloxy)-2-(dimethoxymethyl)pyridin-4(1H)-one obtained in step (b) with N-bromosuccinimide in the presence of a chlorinated solvent to give 3-(benzyloxy)-5-bromo-2-(dimethoxymethyl) pyridin-4(1H)-one of formula V;

d) treating the 3-(benzyloxy)-5-bromo-2-(dimethoxymethyl)pyridin-4(1H)-one obtained in step (c) with n-butyllithium in the presence of dimethylformamide and an ether solvent to give 5-(benzyloxy)-6-(dimethoxymethyl)-4-oxo-1,4-dihydropyridine-3-carbaldehyde of formula VI;

e) reacting the 5-(benzyloxy)-6-(dimethoxymethyl)-4-oxo-1,4-dihydropyridine-3-carbaldehyde obtained in step (d) with sulfamic acid and sodium chlorite in a suitable solvent to give 5-(benzyloxy)-6-(dimethoxymethyl)-4-oxo-1,4-dihydropyridine-3-carboxylic acid of formula VII;

f) condensing the 5-(benzyloxy)-6-(dimethoxymethyl)-4-oxo-1,4-dihydropyridine-3-carboxylic acid obtained in step (e) with 2,4-difluorobenzylamine in the presence of 1-(3-dimethylaminopropyl)-3-ethylcarbodiimide hydrochloride, hydroxybenzotriazole and tertiary amine in a suitable solvent to give 5-(benzyloxy)-N-(2,4-difluorobenzyl)-6-(dimethoxymethyl)-4-oxo-1,4-dihydropyridine-3-carboxamide of formula VIII;

g) condensing the 5-(benzyloxy)-N-(2,4-difluorobenzyl)-6-(dimethoxymethyl)-4-oxo-1,4-dihydropyridine-3-carboxamide obtained in step (f) with allyl bromide in the presence of a base and dimethylformamide to give 1-allyl-5-(benzyloxy)-N-(2,4-difluorobenzyl)-6-(dimethoxymethyl)-4-oxo-1,4-dihydropyridine-3-carboxamide of formula XI;

h) treating the 1-allyl-5-(benzyloxy)-N-(2,4-difluorobenzyl)-6-(dimethoxymethyl)-4-oxo-1,4-dihydropyridine-3-carboxamide obtained in step (g) with formic acid in a ketonic solvent to give 1-allyl-5-(benzyloxy)-N-(2,4-difluorobenzyl)-6-formyl-4-oxo-1,4-dihydropyridine-3-carboxamide of formula XII;

i) reacting the 1-allyl-5-(benzyloxy)-N-(2,4-difluorobenzyl)-6-formyl-4-oxo-1,4-dihydropyridine-3-carboxamide obtained in step (h) with sulfamic acid and sodium chlorite in a suitable solvent to give 1-allyl-3-(benzyloxy)-5-(2,4-difluorobenzyl carbamoyl)-4-oxo-1,4-dihydropyridine-2-carboxylic acid of formula XIII;

j) methylating the 1-allyl-3-(benzyloxy)-5-(2,4-difluorobenzylcarbamoyl)-4-oxo-1,4-dihydropyridine-2-carboxylic acid with methyl iodide in the presence of a base and dimethylformamide to give 1-allyl-3-benzyloxy-5-(2,4-difluoro-benzyl carbamoyl)-4-oxo-1,4-dihydro-pyridine-2-carboxylic acid methyl ester;

k) oxidizing 1-allyl-3-benzyloxy-5-(2,4-difluoro-benzylcarbamoyl)-4-oxo-1,4-dihydro-pyridine-2-carboxylic acid methyl ester with osmium tetraoxide and sodium metaperiodate to give methyl 3-(benzyloxy)-5-(2,4-difluorobenzyl carbamoyl)-4-oxo-1-(2-oxoethyl)-1,4-dihydropyiridine-2-carboxylate;

l) reacting methyl 3-(benzyloxy)-5-(2,4-difluorobenzyl-carbamoyl)-4-oxo-1-(2-oxoethyl)-1,4-dihydropyridine-2-carboxylate with aminobutan-1-ol and acetic acid to yield (4R,12aS)-7-(benzoyloxy)-N-(2,4-difluorobenzyl)-4-methyl-6,8-dioxo-3,4,6,8,12,12a-hexahydro-2H-[1,3]oxazino[3,2-d]pyrido[1,2-a]pyrazine-9-carboxamide; and m) hydrogenating (4R,12aS)-7-(benzoyloxy)-N-(2,4-difluorobenzyl)-4-methyl-6,8-dioxo-3,4,6,8,12,12a-hexahydro-2H-[1,3]oxazino[3,2-d]pyrido[1,2-a]pyrazine-9-carboxamide to yield Dolutegravir.

2. A process for preparing of Dolutegravir of Formula I according to claim 1, the process comprising:

providing Methyl 3-(benzyloxy)-5-(2,4-difluorobenzylcarbamoyl)-4-oxo-1-(2-oxoethyl)-1,4-dihydropyridine-2-carboxylate;

reacting Methyl 3-(benzyloxy)-5-(2,4-difluorobenzylcarbamoyl)-4-oxo-1-(2-oxoethyl)-1,4-dihydropyridine-2-carboxylate with Aminobutane-1-ol and acetic acid to yield (4R,12aS)-7-(benzoyloxy)-N-(2,4-difluorobenzyl)-4-methyl-6,8-dioxo-3,4,6,8,12,12a-hexahydro-2H-[1,3]oxazino[3,2-d]pyrido[1,2-a]pyrazine-9-carboxamide; and hydrogenating (4R,12aS)-7-(benzoyloxy)-N-(2,4-difluorobenzyl)-4-methyl-6,8-dioxo-3,4,6,8,12,12a-hexahydro-2H-[1,3]oxazino[3,2-d]pyrido[1,2-a]pyrazine-9-carboxamide to yield Dolutegravir.

3. A process for the preparation of Dolutegravir of formula I the process comprising:

a) treating the 3-(benzyloxy)-4-oxo-4H-pyran-2-carbaldehyde with trimethyl orthoformate in the presence of camphorsulfonic acid and a suitable solvent to give 3-(benzyloxy)-2-(dimethoxymethyl)-4H-pyran-4-one of formula III;

b) reacting the 3-(benzyloxy)-2-(dimethoxymethyl)-4H-pyran-4-one obtained in step (a) with methanolic ammonia in the presence of an alcoholic solvent to give 3-(benzyloxy)-2-(dimethoxymethyl)pyridin-4(1H)-one of formula IV;

c) brominating the 3-(benzyloxy)-2-(dimethoxymethyl) pyridin-4(1H)-one obtained in step (b) with N-bromosuccinimide in the presence of a chlorinated solvent to give 3-(benzyloxy)-5-bromo-2-(dimethoxymethyl) pyridin-4(1H)-one of formula V;

d) treating the 3-(benzyloxy)-5-bromo-2-(dimethoxymethyl)pyridin-4(1H)-one obtained in step (c) with n-butyllithium in the presence of dimethylformamide and an ether solvent to give 5-(benzyloxy)-6-(dimethoxymethyl)-4-oxo-1,4-dihydropyridine-3-carbaldehyde Formula VI;

e) condensing the 5-(benzyloxy)-6-(dimethoxymethyl)-4-oxo-1,4-dihydropyridine-3-carbaldehyde obtained in step (d) with allyl bromide in the presence of a base and dimethylformamide to give 1-allyl-5-(benzyloxy)-6-(dimethoxymethyl)-4-oxo-1,4-dihydropyridine-3-carbaldehyde of formula IX;

f) reacting the 1-allyl-5-(benzyloxy)-6-(dimethoxymethyl)-4-oxo-1,4-dihydropyridine-3-carbaldehyde obtained in step (e) with sulfamic acid and sodium chlorite in a suitable solvent to give 1-allyl-5-(benzyloxy)-6-(dimethoxymethyl)-4-oxo-1,4-dihydropyridine-3-carboxylic acid of formula X;

g) condensing the 1-allyl-5-(benzyloxy)-6-(dimethoxymethyl)-4-oxo-1,4-dihydropyridine-3-carboxylic acid obtained in step (f) with 2,4-difluorobenzylamine in the presence of 1-(3-dimethylaminopropyl)-3-ethylcarbodiimide hydrochloride, hydroxybenzotriazole and tertiary amine in a suitable solvent to give 1-allyl-5-(benzyloxy)-N-(2,4-difluorobenzyl)-6-(dimethoxymethyl)-4-oxo-1,4-dihydropyridine-3-carboxamide of formula XI;

h) treating the 1-allyl-5-(benzyloxy)-N-(2,4-difluorobenzyl)-6-(dimethoxymethyl)-4-oxo-1,4-dihydropyridine-3-carboxamide obtained in step (g) with formic acid in a ketonic solvent to give 1-allyl-5-(benzyloxy)-N-(2,4-difluorobenzyl)-6-formyl-4-oxo-1,4-dihydropyridine-3-carboxamide of formula XII;

i) reacting the 1-allyl-5-(benzyloxy)-N-(2,4-difluorobenzyl)-6-formyl-4-oxo-1,4-dihydropyridine-3-carboxamide obtained in step (h) with sulfamic acid and sodium chlorite in a suitable solvent to give 1-allyl-3-(benzyloxy)-5-(2,4-difluorobenzylcarbamoyl)-4-oxo-1,4-dihydropyridine-2-carboxylic acid of formula XIII; and j) methylating the 1-allyl-3-(benzyloxy)-5-(2,4-difluorobenzylcarbamoyl)-4-oxo-1,4-dihydropyridine-2-carboxylic acid with methyl iodide in the presence of a base and dimethylformamide to give 1-allyl-3-benzyloxy-5-(2,4-difluoro-benzylcarbamoyl)-4-oxo-1,4-dihydro-pyridine-2-carboxylic acid methyl ester;

k) oxidizing 1-allyl-3-benzyloxy-5-(2,4-difluoro-benzylcarbamoyl)-4-oxo-1,4-dihydro-pyridine-2-carboxylic acid methyl ester with osmium tetraoxide and sodium metaperiodate to give methyl 3-(benzyloxy)-5-(2,4-difluorobenzylcarbamoyl)-4-oxo-1-(2-oxoethyl)-1,4-dihydropyiridine-2-carboxylate;

l) reacting methyl 3-(benzyloxy)-5-(2,4-difluorobenzylcarbamoyl)-4-oxo-1-(2-oxoethyl)-1,4-dihydropyridine-2-carboxylate with aminobutan-1-ol and acetic acid to yield (4R,12aS)-7-(benzoyloxy)-N-(2,4-difluorobenzyl)-4-methyl-6,8-dioxo-3,4,6,8,12,12a-hexahydro-2H-[1,3]oxazino[3,2-d]pyrido[1,2-a]pyrazine-9-carboxamide; and m) hydrogenating (4R,12aS)-7-(benzoyloxy)-N-(2,4-difluorobenzyl)-4-methyl-6,8-dioxo-3,4,6,8,12,12a-hexahydro-2H-[1,3]oxazino[3,2-d]pyrido[1,2-a]pyrazine-9-carboxamide to yield Dolutegravir.

4. A process for preparing of Dolutegravir of Formula I according to claim 3, the process comprising:

providing Methyl 3-(benzyloxy)-5-(2,4-difluorobenzylcarbamoyl)-4-oxo-1-(2-oxoethyl)-1,4-dihydropyridine-2-carboxylate;

reacting Methyl 3-(benzyloxy)-5-(2,4-difluorobenzylcarbamoyl)-4-oxo-1-(2-oxoethyl)-1,4-dihydropyridine-2-carboxylate with Aminobutane-1-ol and acetic acid to yield (4R,12aS)-7-(benzyloxy)-N-(2,4-difluorobenzyl)-4-methyl-6,8-dioxo-3,4,6,8,12,12a-hexahydro-2H-[1,3]oxazino[3,2-d]pyrido[1,2-a]pyrazine-9-carboxamide; and hydrogenating (4R,12aS)-7-(benzoyloxy)-N-(2,4-difluorobenzyl)-4-methyl-6,8-dioxo-3,4,6,8,12,12a-hexahydro-2H-[1,3]oxazino[3,2-d]pyrido[1,2-a]pyrazine-9-carboxamide to yield Dolutegravir.

\* \* \* \* \*